United States Patent [19]

Hunter et al.

[11] Patent Number: 4,647,708
[45] Date of Patent: Mar. 3, 1987

[54] METAL LEACH CONTROL FROM PROCESSES WITH POLYMER-SUPPORTED CATALYSTS

[75] Inventors: Douglas L. Hunter; Stanley E. Moore; Gordon G. Willis, all of Lake Jackson, Tex.

[73] Assignee: The Dow Chemical Company, Midland, Mich.

[21] Appl. No.: 801,184

[22] Filed: Nov. 25, 1985

[51] Int. Cl.$^4$ ............................................. C07C 29/16
[52] U.S. Cl. ..................................... 568/883; 568/451
[58] Field of Search .............. 568/817, 838, 455, 883, 568/451

[56] References Cited

U.S. PATENT DOCUMENTS

| | | | |
|---|---|---|---|
| 3,594,425 | 7/1971 | Braden et al. | 568/455 |
| 4,098,727 | 7/1978 | Haag et al. | 568/455 |
| 4,178,314 | 12/1979 | Carlock | 568/455 |
| 4,179,403 | 12/1979 | Kim | 568/455 |
| 4,189,448 | 2/1980 | Carlock | 568/455 |
| 4,198,353 | 4/1980 | Carlock | 568/455 |
| 4,317,936 | 3/1982 | Kim | 568/455 |

Primary Examiner—Werren B. Lone
Attorney, Agent, or Firm—B. G. Colley

[57] ABSTRACT

A method of controlling metal leaching in heterogeneous catalysis conducted in the presence of a solid-supported, metal complex catalyst with liquid feed subject to inclusion of ligands competitive with the solid support for the metal complex. The method is specifically applicable where the heterogeneous catalysis reaction is a combined hydroformylation/reduction reaction producing aldehydes and alcohols from olefins.

19 Claims, 1 Drawing Figure

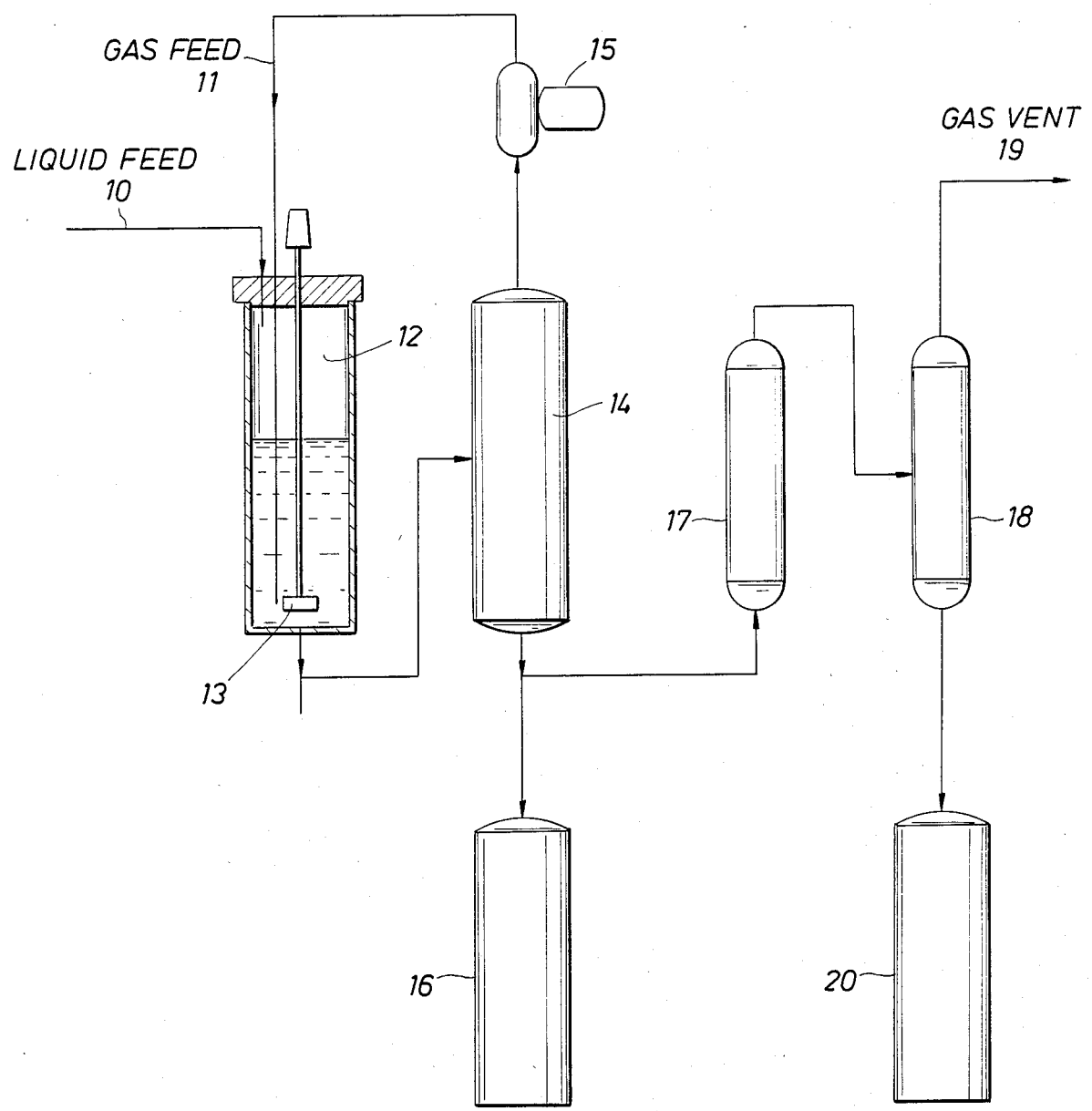

4,647,708

METAL LEACH CONTROL FROM PROCESSES WITH POLYMER-SUPPORTED CATALYSTS

FIELD OF THE INVENTION

This invention relates to the production of aldehydes and alcohols by the hydroformylation/reduction reaction of olefins with hydrogen and carbon monoxide in the presence of a metal complex catalyst supported by a polymer or resin where metal leaching of the catalyst is encountered.

BACKGROUND OF THE DISCLOSURE

The reaction of an olefin with hydrogen and carbon monoxide to produce alcohols is the well known hydroformylation/reduction reaction also known as the oxo reaction. When using homogeneous catalysis with metal containing catalysts, soluble in the liquid reaction mixture during the hydroformylation/reduction reaction, there is a necessary recovery and regeneration cost for the dissolved metal catalyst due to the expense of the metal itself and the need to minimize the loss of such metal. Even with sophisticated recovery methods small losses of metal still occur, thus the economic use of homogeneous catalysis using a metal containing catalyst is limited.

Heterogeneous catalysis can be used in the oxo reaction by deploying a catalyst containing transition metal complexes supported upon solid polymers or resins. However, the problem with metal leaching from the solid supported catalyst is still a major consideration due to the cost of recovery or replacement of the catalyst. This metal leaching occurs because some species in the oxo process are better ligands, forming a stronger bond with the metal complex than the ligand functionality of the solid support. A growing recognition of the problem of metal loss due to solubility and leaching from the catalyst is demonstrated by the following prior art. Pruett et al, *Journal of Organic Chemistry*, Volume 34, page 327, (February, 1969) teaches a catalyst composed of a transition metal complex supported on a solid support, but the complex is soluble in the liquid reaction mixture. U.S. Pat. No. 3,352,924 discloses use of a crystalline alumino-silicate as a solid support for the catalyst, but this catalyst tends to lose effectiveness over time in a continuous operation. U.S. Pat. No. 3,487,112 has disclosed use of transition metal complexes deposited on inert solids, but again the complexes are soluble in the liquid reaction mixture. Haag et al, U.S. Pat. No. 4,098,727 teaches use of a polymer as a solid support for transition metal complexes which then are insoluble in the liquid reaction mixture, due to strong chemical bonds between the polymer and the metal complex. However, in the presence of competing liquid species in the process, the metal complex may be exchanged from the polymer bond to the competing species thus becoming soluble in the liquid reaction mixture. Garrou et al, U.S. Pat. No. 4,262,147 and Hartwell et al, U.S. Pat. No. 4,144,191 discuss applications of transition metal complexes supported by polymers, but do not address the problem of metal leaching from the catalyst.

One aspect of the discovery of the present invention is that control of the species concentration in the oxo process which species is a competing ligand with the catalyst solid support for the metal complex enables this invention to reduce metal leach. In addition, the present invention discloses that when ligand species present invention discloses that when ligand species concentration is favorable, metal leach is further controlled by use of a continuous stirred tank reactor or recirculation reactor as opposed to a single-pass fixed bed reactor. This invention is a process continuously run in such a way as to control metal leach from reactors loaded with a catalyst wherein the transition metal complex catalyst is bound to a solid polymer or resin support. These and other features will become more readily apparent on review of the disclosure described below.

DETAILED DESCRIPTION OF THE APPARATUS

The single drawing is a flow chart showing an embodiment of apparatus useful in performing the present process. Attention is directed to the drawing, a flow chart of the process of this disclosure. The drawing shows in flow chart format the oxo process utilizing a hydroformylation/reduction reaction in a continuous stirred tank reactor miniplant. This drawing enables the features, advantages, and objects of the present invention to be more readily understood. The olefin liquid feed 10 and CO and $H_2$ gaseous reactants 11 are fed to a continuously stirred tank reactor 12, containing the solid supported metal complex catalyst 13. The product of this reactor is then discharged to a gas-liquid separator 14 by siphon flow maintained by the liquid level within the separator. Gases from the separator 14 are recycled to the reactor through a line and pump 15. The liquid from the separator 14 is either stored in a tank 16 or further processed through a fixed bed, liquid full reactor 17 and then delivered into another gas-liquid separator 18. The gas line 19 vents the separator 18 while the separated liquid is then stored in a tank 20.

DESCRIPTION OF PROCESS AND PRODUCT MADE THEREBY

Alcohols and aldehydes can be obtained from olefins by the oxo process. In the presence of the proper catalyst, olefins react with carbon monoxide and hydrogen to yield aldehydes. The preferred ratio of $CO/H_2$ of this invention is ½. During the oxo process the olefin will attach to the catalyst as a ligand, later to break off with the addition of a formyl group to the olefin, thus producing an aldehyde. These aldehydes can be readily reduced by catalytic hydrogenation to alcohols. The classic oxo catalyst is a transition metal carbonyl formed by a reaction of the transition metal with carbon monoxide. Pressures from about 500 psi to about 20,000 psi have been used in oxo processes. The preferred pressure of the present invention is about 4,000 psi. Temperatures from about 80° C. to about 220° C. are used in the oxo process of this invention. When rhodium is used in the transition metal catalyst, the preferred concentration is at least 25 ppm of rhodium for effective catalyst action. The catalyst solid support may be a functionalized polymer or resin such as a tertiary amine functionalized resin.

An important problem when using a homogeneous catalyst soluble in the liquid reaction mixture is catalyst metal loss. One approach to solving this problem has been to anchor, support, or bond the catalyst to a solid support through a ligating functionality on the support. This heterogeneous catalysis is used to prevent metal loss. However, some metal is still leached from the solid supported catalyst, thus requiring recovery of the metal. Some species in the process whether starting material, product, by-product, intermediate, or solvent, is a better ligand, forming a stronger bond with the metal complex than the ligating functionality of the support. The metal complex is therefore leached out of the solid support and dissolved in the liquid reaction mixture. This causes greater economic cost for recovery, especially due to the high cost of some transition metals selected for the catalyst such as rhodium. In the past, the oxo process has been limited to a batch configuration in order to minimize metal loss.

This invention is based on two features that help control metal leach: (1) ligating species that compete with the solid support ligand for the metal catalyst are maintained at a low concentration, and (2) the use of continuous stirred tank reactors or recirculation reactors.

The advantage of continuous stirred tank reactors or recirculation reactors over a single-pass, fixed-bed reactor is that the metal is continuously redistributed over the support as opposed to washing the metal out of the reactor. By controlling the concentration of the species acting as a competing ligand in the process and using continuous stirred tank reactors or recirculation reactors as opposed to a single-pass, fixed-bed reactor, the amount of metal leach in the present invention coming out of the reactor system will be reduced to the extent that it is feasible economically to operate the process continuously rather than in batch configuration. Running in such a batch configuration is not practical in commercial use currently.

The question of reactor choice is based upon constraints existing in an oxo reaction; there are sequential reactions with multiple pathways to the final product and the amount of catalyst leach is dependent upon the predominant species in the reactor at a given time. In the prior art, a semi-batch reactor has been considered necessary because the catalyst metal returned to the solid support at the completion of the combined hydroformylation/reduction reaction. As mentioned before, this batch configuration has placed a severe restriction on the commercial use of this process.

Aldehydes are created from olefins in the hydroformylation step and then further reacted to produce alcohols in the reduction step. Alcohols are weaker ligands than their corresponding aldehydes or olefins in relation to ligating and leaching the transition metal complex of an oxo catalyst. Therefore, the concentration of alcohols must be raised in a hydroformylation/reduction reaction in order to control metal leach, and vice versa, the concentration of olefins and aldehydes must be reduced. After the hydroformylation reaction, the further reduction reaction is carried out to form alcohols from aldehydes by addition of $H_2$. By increasing the yield of alcohols, the aldehyde and olefin concentrations are reduced and leaching is restrained.

A factor in selecting the type of reactor best suited for this process is the reaction sequence. The aldehyde intermediates require time to convert to alcohols and offer problems if they remain as impurities in the product alcohol. Therefore, a viable alternative to a semi-batch reactor is to convert olefins to aldehydes in one reactor and then convert the aldehydes to alcohols in a second reactor. Increasing the concentration of the alcohol favors the metal catalyst being bound to the solid support. These factors lead to the use of a continuous stirred tank reactor for a primary reactor converting the olefin to a mixture of aldehydes and alcohols. That mixture is then converted to alcohols in a second reactor.

The following examples will be illustrative of certain specific embodiments of the invention.

EXAMPLE 1

A 10 gm sample of pretreated resin, $Rh_4(CO)_{12}$, supported upon Amberlite ® IRA-68, was charged to a 100 ml flask. The resin was then refluxed with 10 gm of various components in toluene that occur in dicyclopentadiene dimethanol production. A sample of the liquid was taken after refluxing for ½ hr and analyzed for rhodium. The results are given in Table 1; tendencies to leach rhodium from the catalyst are shown of various components occurring in a combined hydroformylation/reduction reaction to produce dicyclopentadiene dimethanol. It is important to note that significantly more rhodium is leached by olefins and aldehydes than alcohols. Therefore one means of controlling catalyst leach is to lower the concentration of olefins and aldehydes while increasing the concentration of alcohols in the process. It was apparent that the alcohols were not good ligands since they did not bring the metal into solution.

TABLE 1

| Rhodium Leach in Dicyclopentadiene Dimethanol Production | |
|---|---|
| Substrate | Rh ppm |
| Toluene | .0 |
| THF | 0.36 |
| *CO/H$_2$ | 1.24 |
| Dicyclopentadiene | 12.44 |
| Dicyclopentadiene Monoaldehyde | 19.42 |
| Dicyclopentadiene Monomethanol | 5.85 |
| Dicyclopentadiene Dialdehyde | 11.02 |
| Dicyclopentadiene Dimethanol | 0.24 |

*Reactor under 3000 psi, 130° C.

EXAMPLE 2

A 2 liter continuous stirred tank autoclave was charged with 106 gm of a dried tertiary amine resin such as Dowex ® MWA-1 manufactured by The Dow Chemical Company, 0.8 gm $Rh_2O_3$, 800 ml toluene and 300 ml tetrahydrofuran. The autoclave was maintained at 120° C. and 4,000 psi. The atmosphere inside the autoclave was comprised of gaseous reactants $CO/H_2$ in a ratio of ½. A 20% dicyclopentadiene (DCPD) solution in toluene/tetrahydrofuran (85/15 weight percent ratio) was fed to the autoclave at 175 ml/hr to give a residence time of 6.3 hours. After further processing through a gas/liquid separator, the effluent from the first autoclave was introduced into a second autoclave. The second autoclave was maintained at 120° C. and 4,000 psi and a residence time of about 1 hr was used. A charge of 53 gm of Dowex ® MWA-1 resin and 0.4 gm $Rh_2O_3$ was placed in this second autoclave. The dissolved gasses remaining in the effluent from the first autoclave were sufficient for the conversion required in the second autoclave. The composition of this reactor system over a 30 day run is shown in Table 2. The significant rhodium leach data shows very low Rh ppm values maintained in this system even when the aldehyde concentration increased overtime.

TABLE 2

| REACTOR OUTPUT COMPOSITION OVERTIME | | | | | | |
|---|---|---|---|---|---|---|
| Time hr | % DCPD MA | % DCPD MM | % DCPD DA | % DCPD MM/MA | % DCPD DM | ppm Rh |
| 49 | 4 | 3 | 1 | 5 | 85 | 1.4 |
| 240 | 4 | 5 | 2 | 7 | 81 | >1 |

TABLE 2-continued

REACTOR OUTPUT COMPOSITION OVERTIME

| Time hr | % DCPD MA | % DCPD MM | % DCPD DA | % DCPD MM/MA | % DCPD DM | ppm Rh |
|---|---|---|---|---|---|---|
| 408 | 3 | 6 | 3 | 10 | 76 | >1 |
| 553 | 3 | 6 | 5 | 13 | 73 | 2.4 |
| 676 | 2 | 7 | 7 | 16 | 68 | 1.5 |
| 765 | 2 | 7 | 7 | 19 | 65 | 1.2 |

DCPD MA - dicyclopentadiene monoaldehyde
DCPD MM - dicyclopentadiene monomethanol
DCPD DA - dicyclopentadiene dialdehyde
DCPD MM/MA - dicyclopentadiene monomethanol/monoaldehyde
DCPD DM - dicyclopentadiene dimethanol

EXAMPLE 3

The same process as shown in Example 2 was carried out in a semi-batch process rather than in continuous configuration. The product was drained and fresh feed recharged to the reactor, but the same solid supported catalyst was maintained for each batch. The rhodium leach concentrations varied from 5.2 to 8.3 ppm over 32 sequential batches. Clearly the batch configuration led to a higher leach than the continuous process of Example 2.

While the foregoing is directed to the preferred embodiment of the present invention, other and further embodiments of the invention may be devised without departing from the basic scope thereof, and the scope thereof is determined by the claims which follow.

What is claimed is:

1. A method of controlling metal leaching in heterogeneous catalysis assisted reaction being a combined hydroformylation/reduction reaction conducted in the presence of a solid-supported, metal complex catalyst with liquid feed and wherein the reaction is subject to ligands competitive with the solid support for the metal complex, the method comprising the steps of:
   (a) reacting the liquid feed with the required CO and $H_2$ in the presence of a solid-supported, metal complex catalyst in a reactor to provide catalysis assistance to a combined hydroformylation/reduction reaction; and
   (b) maintaining below specified limits the concentration of any ligands that compete with the solid support for the metal complex to thereby reduce leaching of the catalyst to competing ligands while conducting the combined hydroformylation/reduction reaction.

2. The method of claim 1 wherein said hydroformylation/reduction reaction has a $CO/H_2$ stoichiometric ratio of $\frac{1}{2}$.

3. The method of claim 1 wherein the hydroformylation/reduction reaction forms aldehydes and alcohols from an olefin liquid feed.

4. The method of claim 3 wherein an olefin in the liquid feed is dicyclopentadiene.

5. The method of claim 1 wherein the competing ligands are rendered noncompetitive with the solid support by a further reaction of the ligating species.

6. The method of claim 5 wherein competing ligands are aldehydes and are controlled by reacting such ligands with $H_2$ to form alcohols which are weaker ligands than the corresponding aldehydes.

7. The method of claim 1 wherein the competing ligands are rendered noncompetitive with the solid support by employing a higher concentration of the remaining nonligating species.

8. The method of claim 1 wherein the liquid feed is initially processed to reduce competing ligand concentrations while raising concentrations of the remainder of said liquid feed components.

9. The method of claim 1 including the step of conducting the catalysis reaction is separated reactors to reduce metal leach.

10. The method of claim 1 wherein the reaction is conducted in a continuous stirring tank reactor.

11. The method of claim 1 wherein the reaction is conducted in a recirculation reactor.

12. The method of claim 3 wherein the pressure in the reactor is between 500 and 20,000 psig.

13. The method of claim 3 wherein the pressure in the reactor is 4,000 psig.

14. The method of claim 3 wherein the temperature in the reactor is between 80° C. and 220° C.

15. The method of claim 1 wherein the catalyst is selected from the group consisting of rhodium complexes and rhodium/cobalt complexes.

16. The method of claim 1 wherein the catalyst solid support is a functionalized polymer.

17. The method of claim 1 wherein the catalyst solid support is an amine functionalized resin.

18. The method of claim 1 wherein the catalyst solid support is a tertiary amine functionalized resin.

19. The method of claim 1 wherein competing ligands in the feed are aldehydes.

* * * * *